(12) United States Patent
Van Antwerp et al.

(10) Patent No.: US 6,280,416 B1
(45) Date of Patent: Aug. 28, 2001

(54) CONSTANT FLOW MEDICATION INFUSION PUMP

(75) Inventors: William P. Van Antwerp, Valencia Hills; Susan M. McConnell, Woodland Hills; Peter C. Lord, Santa Clarita, all of CA (US)

(73) Assignee: MiniMed Inc., Northridge, CA (US)

( * ) Notice: Subject to any disclaimer, the term of this patent is extended or adjusted under 35 U.S.C. 154(b) by 0 days.

(21) Appl. No.: 09/253,382

(22) Filed: Feb. 19, 1999

(51) Int. Cl.[7] ................................................... A61M 37/00
(52) U.S. Cl. ...................... 604/141; 604/891.1; 604/132; 128/DIG. 12
(58) Field of Search ............................. 604/891.1, 890.1, 604/132, 140, 141, 142, 93, 93.01, 131; 128/DIG. 12

(56) References Cited

U.S. PATENT DOCUMENTS

| 3,731,681 | 5/1973 | Blackshear et al. ................. 128/214 |
| 3,951,147 | 4/1976 | Tucker et al. ......................... 128/260 |
| 4,140,122 | * 2/1979 | Kuhl et al. . |
| 4,668,231 | * 5/1987 | De Vries et al. .................. 604/891.1 |
| 4,820,273 | * 4/1989 | Reinicke .............................. 604/141 |
| 4,969,873 | * 11/1990 | Steinbach et al. ..................... 604/93 |
| 5,085,656 | * 2/1992 | Polashegg ........................ 604/891.1 |
| 5,167,633 | * 12/1992 | Mann et al. ......................... 604/141 |
| 5,318,540 | * 6/1994 | Athayde et al. ..................... 604/141 |
| 5,514,103 | 5/1996 | Srisathapat et al. ................. 604/141 |
| 5,527,307 | 6/1996 | Srisathapat et al. ............... 604/892.1 |
| 5,607,418 | * 3/1997 | Arzbaecher ....................... 604/891.1 |
| 5,722,957 | * 3/1998 | Steinbach ........................... 604/141 |
| 5,766,150 | * 6/1998 | Langkau ............................... 604/93 |
| 5,769,823 | * 6/1998 | Otto .................................... 604/141 |
| 5,785,688 | * 7/1998 | Joshi et al. .......................... 604/141 |
| 5,814,019 | * 9/1998 | Steinbach et al. ................... 604/131 |
| 5,908,414 | * 6/1999 | Otto et al. ........................ 604/891.1 |
| 5,957,890 | * 9/1999 | Mann et al. ......................... 604/131 |

FOREIGN PATENT DOCUMENTS

| 0488701 | 6/1992 | (EP) . |
| 9740873 | 11/1997 | (WO) . |

OTHER PUBLICATIONS

EPA, "http://www.epa.gov/ozone/", 23 pages, see entire collection.*

* cited by examiner

Primary Examiner—Anhtuant T. Nguyen
Assistant Examiner—Michael M. Thompson
(74) Attorney, Agent, or Firm—Gates & Cooper LLP

(57) ABSTRACT

A medication infusion pump includes a housing, a medication chamber defined within the housing, a medication delivery device in fluid communication with the medication chamber, a propellant chamber defined within the housing and adapted to apply a predetermined positive pressure to a medication in the medication chamber, and a non-ozone depleting, non-toxic propellant within the propellant chamber. The propellant preferably has a vapor pressure between about 11 psig and about 50 psig at 37° C.

12 Claims, 2 Drawing Sheets

CONSTANT FLOW MEDICATION INFUSION PUMP

FIELD OF THE INVENTION

The present invention relates to medication infusion pumps for controlled delivery of a selected medication to a patient over an extended period of time.

BACKGROUND OF THE INVENTION

Medication infusion pumps that supply a medication to a patient at a substantially constant flowrate are known. Exemplary infusion pumps are described in U.S. Pat. No. 3,731,681, to Blackshear; U.S. Pat. No. 3,951,147, to Tucker et al.; U.S. Pat. No. 5,167,633, to Mann et al.; and U.S. Pat. No. 5,722,957, to Steinbach. Modern infusion pumps have been developed that are implantable into the body of a patient, particularly a human patient, to whom the medication is to be supplied.

Known infusion pumps typically include a housing that contains a medication chamber and a propellant chamber, together with appropriate means for loading the selected medication into the medication chamber and for supplying the medication to the patient. The propellant chamber typically contains a gaseous or liquid/vapor propellant at a pressure above atmospheric pressure, and applies a predetermined positive pressure to the medication within the medication chamber. This affords a substantially continuous and constant flow of the medication to the patient.

Modern environmental concerns mandate that propellants employed in the foregoing infusion pumps, as well as other devices requiring propellants, be environmentally benign. It is of particular concern to avoid propellants that have an adverse effect on ozone.

A need exists for a medication infusion pump that employs an improved propellant. It would be particularly desirable to provide a medication infusion pump that employs a propellant that is not ozone-depleting.

SUMMARY OF THE PREFERRED EMBODIMENTS

In accordance with one aspect of the present invention, there is provided a medication infusion pump that includes a housing, a medication chamber defined within the housing, a medication delivery device in fluid communication with said medication chamber, a propellant chamber defined within the housing and adapted to apply a predetermined positive pressure to a medication in the medication chamber, and a propellant within the propellant chamber. The propellant preferably has a vapor pressure between about 11 psig and about 50 psig at 37° C., and is non-ozone-depleting and non-toxic.

A mixture of two or more propellants, or of a propellant and one or more diluent gases, can also be employed.

In a preferred embodiment, the propellant is a gas selected from the group consisting of HFA-134a, HCFC-141b and neopentane.

In accordance with another aspect of the invention, there is provided a medication infusion pump that dispenses a medication at a substantially constant flowrate by application to the medication of a predetermined positive pressure. The predetermined positive pressure is exerted by a non-ozone depleting, non-toxic propellant having a vapor pressure between about 11 psig and about 50 psig at 37° C.

In accordance with another aspect of the present invention, there is provided a method of supplying a medication to a patient from a medication infusion pump as described herein. The method includes the steps of filling the propellant chamber with a non-ozone-depleting, non-toxic propellant having a vapor pressure between about 11 psig and about 50 psig at 37° C., and dispensing the medication from the medication chamber.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

The invention may be more readily understood by referring to the accompanying drawing in which.

DETAILED DESCRIPTION OF THE PREFERRED EMBODIMENTS

Figure 1:
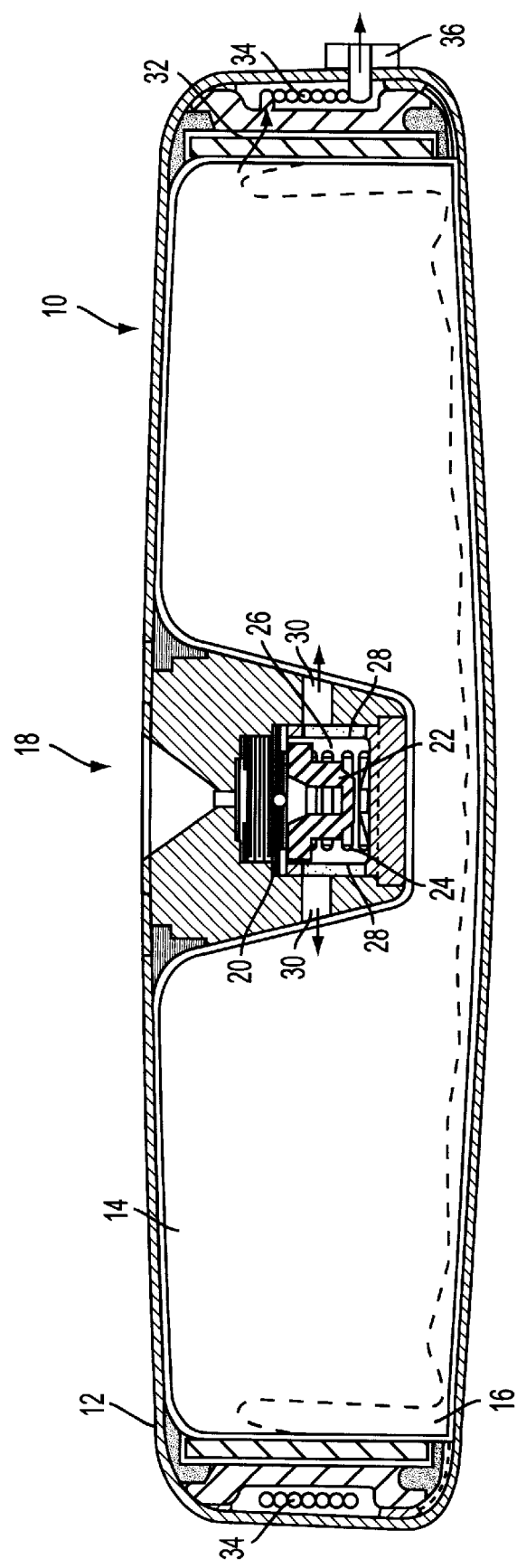
FIG. 1 is a schematic representation of a first embodiment of a medication infusion pump according to the present invention.

The propellents according to the present invention can be supplied to any type of infusion pump that employs a propellant or propellant mixture having a pressure above ambient pressure at 37° C. Such infusion pumps include those disclosed in U.S. Pat. Nos. 3,731,681; 3,951,147; 5,167,633; and 5,722,957; as well as the constant flow-type infusion pumps described in copending, commonly assigned U.S. patent application Ser. No. 08/871,830, filed Jun. 9, 1997. The foregoing patent application and issued U.S. patents are incorporated in their entireties herein by reference.

Propellants are "non-toxic" for the purposes of this invention if they comply with the standard established in ISO 10993. Propellants are also "non-toxic" for the purposes of this invention if they are included in the inventory of the Toxic Substances Control Act.

A propellants is considered "non-ozone depleting" for the purposes of this invention if (i) the propellant has an Ozone Depletion Potential (ODP) less than 1.0, more preferably less than about 0.10 (with the ODP of CFC-11=1.0) and either (ii) the propellant is not a Class I or Class II controlled substance as set forth in 40 C.F.R. Part 82, Subpart A, or (iii) the propellant is subject to the exemption provided for under 40 C.F.R. §82.4(s)(1) (use in a medical device). Determination of the ODP of a propellant is readily carried out by those skilled in the art.

Propellants useful according to the present invention preferably have a vapor pressure between about 11 psig and about 50 psig at 37° C., more preferably between 20 psig and 24 psig at 37° C.

Exemplary useful propellants include hydrochlorofluorocarbons (HCFC's) and hydrofluoroalkanes (HFA's) such as HCFC-141b (chemical formula $CCl_2FCH_3$) and HFA-134a (chemical formula $CH_2F-CF_3$); $C_3F_8$; $SF_6$; and neopentane.

Other propellants that are useful according to the invention include additional perfluorocarbons (PFC's) such as perfluorobutane and perfluoropentane; hexafluoro-1,3-butadiene; 1,1,1,2,3,3-hexafluoropropane; and octafluoro-2-butene. It should be noted that certain of the foregoing propellants, such as hexafluoro-1,3-butadiene, must be handled with care. However, since the propellants are typically sealed within the propellant chamber of the inventive pump, the use of such propellants in the present invention is not believed to represent a hazard.

The propellant employed according to the present invention can be a single propellant, such as HCFC-141b or neopentane. In the alternative, propellant blends ("precision mixtures") can also advantageously be employed. For example, a precision mixture can be prepared in order to reduce the rate of diffusion of the mixture across a barrier separating the propellant and medication chambers of the pump, or to reduce any potential combustion hazard associated with the selected propellant. Useful precision mixtures include, for example, neopentane+$O_2$, neopentane+$N_2$, neopentane+$O_2$+$N_2$, neopentane+$CO_2$. Precision mixtures including noble gases such as Ar, Xe and He can also advantageously be prepared, for example to increase the vapor pressure of the mixture.

In selecting a propellant or propellant mixture according to the invention, care must be taken to avoid adverse interactions between the propellant(s) and components of the infusion pump, particularly membranes that separate the propellant chamber from the medication chamber. For example, when flexible polymeric membranes are employed, propellants that act as solvents for the polymeric material must be avoided. In the alternative, membranes that are resistant to the selected propellant(s) can be used. For example, the surface of the membrane in contact with the propellant(s) can be metallized.

Referring now to the drawings, in FIG. 1 a schematic representation of a first embodiment of a medication infusion pump 10 according to the invention includes a housing 12 within which a medication chamber 14 and a propellant chamber 16 are defined. The selected propellant or propellant mixture is supplied to propellant chamber 16 by conventional means known to those skilled in the art.

As shown in FIG. 1, propellant chamber 16 is a flexible and expansible bag formed from a polymeric material and secured within housing 12. When medication chamber 14 is filled with the selected medication, propellant chamber 16 assumes a collapsed state (shown dashed). As the medication is supplied from pump 10, propellant chamber 16 gradually expands until it occupies substantially all of the interior volume within housing 12 (shown in solid line), and medication chamber 14 correspondingly decreases in volume.

A medication is loaded into medication chamber 14, for example, via fitting 18 adapted to receive a hypodermic needle (not shown). The hypodermic needle is inserted into fitting 18 through septum 20 and urges hollow valve 22 downwardly against valve return spring 24. The medication flows from the hypodermic needle out of valve 22 into reservoir 26 and subsequently through filters 28 and medication chamber inlets 30 into medication chamber 14. When the hypodermic needle is withdrawn, valve return spring 24 urges valve 22 upward, closing fitting 18. The medication is then delivered from medication chamber 14 through filters and capillary tube 34, which is wound around the inner circumference of housing 12 before being supplied to a patient via outlet 36.

Figure 2:
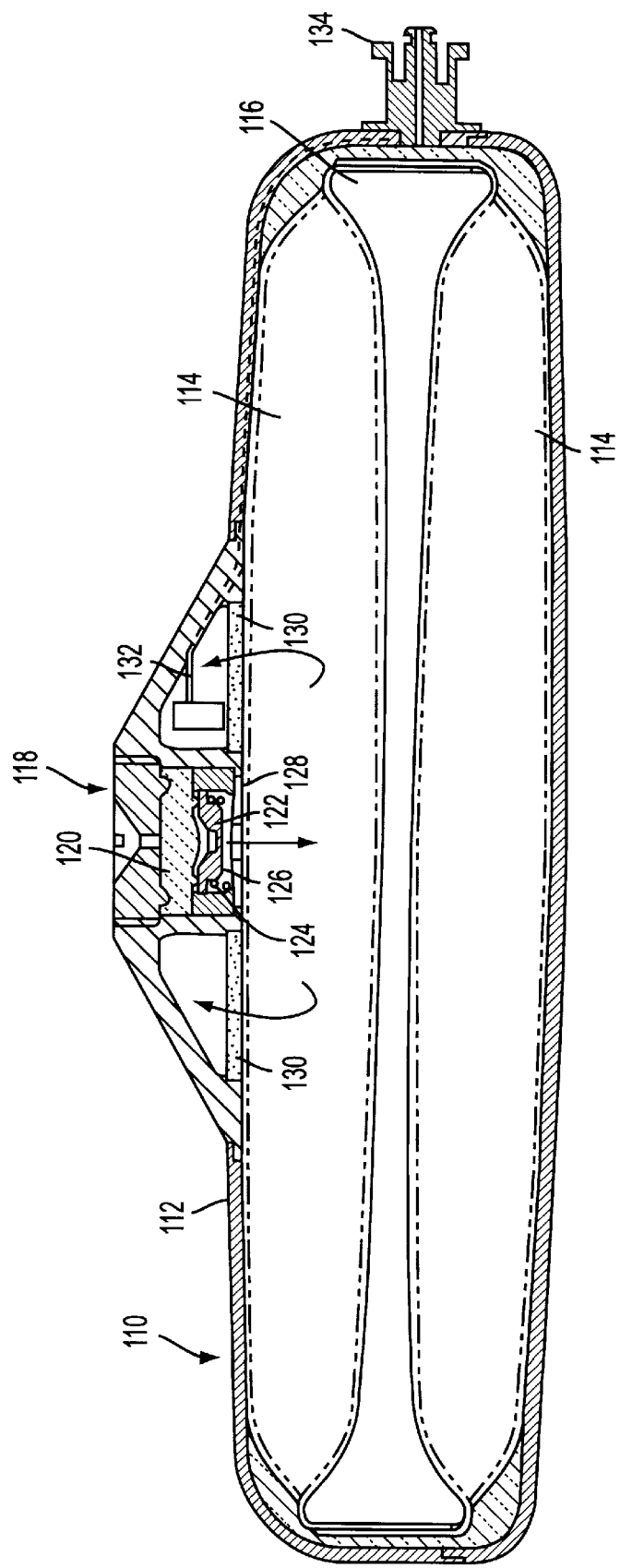
FIG. 2 is a schematic representation of a second embodiment of a medication infusion pump according to the present invention.

In FIG. 2, an alternative infusion pump 110 includes a propellant chamber 116 that is defined across the interior of housing 112. The propellant chamber 116 expands from its collapsed state (shown dashed) as medication is supplied from medication chamber 114, defined on either side of propellant chamber 116. Medication is supplied to the medication chamber 114 through fitting 118 via a hypodermic needle, in a manner similar to the previous embodiment. The hypodermic needle is inserted through septum 1 20 and urges valve 1 22 downward against valve return spring 124, permitting the medication to flow from reservoir 126 through filter 128 into medication chamber 114. From medication chamber 114 the medication is supplied to the patient via filters 130 and capillary tube 132 to outlet 134, similarly to the previous embodiment.

Other known ways of defining a propellant chamber within a medication infusion pump can also be employed.

What is claimed is:

1. A medication infusion pump comprising a) a housing, b) a medication chamber defined within said housing, c) a medication delivery device in fluid communication with said medication chamber, d) a propellant chamber defined within said housing and adapted to apply predetermined positive pressure to a medication within said medication chamber, and e) a non-ozone depleting, non-toxic propellant within said propellant chamber.

2. The medication infusion pump of claim 1 wherein said propellant has a vapor pressure between about 11 psig and about 50 psig at 37° C.

3. The medication infusion pump of claim 2 wherein said propellant has a vapor pressure between about 20 psig and about 24 psig at 37° C.

4. The medication infusion pump of claim 1 wherein said propellant is selected from the group consisting of HFA-134a, HCFC-141b and neopentane.

5. The medication infusion pump of claim 1 wherein said propellant is selected from the group consisting of HFA-134a and HCFC-141b.

6. The medication infusion pump of claim 1 comprising a mixture of at least two propellants.

7. The medication infusion pump of claim 1 comprising at least one propellant in admixture with at least one diluent gas.

8. The medication infusion pump of claim 7 wherein said diluent is selected from the group consisting of $O_2$, $N_2$, $CO_2$, Ar, Xe and He.

9. A medication infusion pump that dispenses a medication at a substantially constant flowrate by application to said medication of a predetermined positive pressure, wherein said pressure is exerted by a non-ozone depleting, non-toxic propellant having a vapor pressure between about 11 psig and about 50 psig at 37° C.

10. The medication infusion pump of claim 9 wherein said propellant has a vapor pressure between about 20 psig and about 24 psig at 37° C.

11. The medication infusion pump of claim 9 wherein said propellant is selected from the group consisting of HFA-134a, HCFC-141b and neopentane.

12. The medication infusion pump of claim 11 wherein said propellant is selected from the group consisting of HFA-134a and HCFC-141b.

* * * * *